(12) United States Patent
Miller (10) Patent No.: US 8,080,040 B2
(45) Date of Patent: Dec. 20, 2011

(54) ANCHOR WITH TWO MEMBER SECURING MECHANISM FOR ATTACHING AN ELONGATED MEMBER TO A BONE

(75) Inventor: Keith E. Miller, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 411 days.

(21) Appl. No.: 12/260,823

(22) Filed: Oct. 29, 2008

(65) Prior Publication Data

US 2010/0106189 A1   Apr. 29, 2010

(51) Int. Cl.
*A61B 17/70* (2006.01)
(52) U.S. Cl. .................... 606/272; 606/265; 606/279
(58) Field of Classification Search .......... 606/250–278, 606/279; 411/508, 913, 45, 46
See application file for complete search history.

(56) References Cited

U.S. PATENT DOCUMENTS

| | | | |
|---|---|---|---|
| 5,346,493 A | 9/1994 | Stahurski et al. | |
| 5,554,157 A | 9/1996 | Errico et al. | |
| 5,683,390 A | 11/1997 | Metz-Stavenhagen et al. | |
| 5,882,350 A | 3/1999 | Ralph et al. | |
| 6,077,262 A | 6/2000 | Schlapfer et al. | |
| 6,090,111 A | 7/2000 | Nichols | |
| 6,302,888 B1 | 10/2001 | Mellinger et al. | |
| 6,440,132 B1 | 8/2002 | Jackson | |
| 6,471,705 B1 | 10/2002 | Biedermann et al. | |
| 6,478,797 B1 | 11/2002 | Paul | |
| 6,540,749 B2 | 4/2003 | Schafer et al. | |
| 6,585,737 B1 | 7/2003 | Baccelli et al. | |
| 6,730,089 B2 | 5/2004 | Jackson | |
| 6,740,086 B2 * | 5/2004 | Richelsoph | 606/60 |
| 6,843,791 B2 | 1/2005 | Serhan | |
| 7,204,838 B2 | 4/2007 | Jackson | |
| 7,744,636 B2 * | 6/2010 | Richelsoph | 606/272 |
| 7,763,049 B2 * | 7/2010 | Roychowdhury | 606/246 |
| 7,811,310 B2 * | 10/2010 | Baker et al. | 606/267 |
| 2001/0012937 A1 | 8/2001 | Schaffler-Wachter et al. | |
| 2005/0033296 A1 | 2/2005 | Bono et al. | |
| 2005/0277924 A1 * | 12/2005 | Roychowdhury | 606/61 |
| 2006/0025768 A1 * | 2/2006 | Iott et al. | 606/61 |
| 2006/0095037 A1 | 5/2006 | Jones et al. | |

(Continued)

FOREIGN PATENT DOCUMENTS

WO   WO 2008/024937   *   2/2008

*Primary Examiner* — Eduardo C Robert
*Assistant Examiner* — Jan Christopher Merene (57) ABSTRACT

A device to attach an elongated member to a bone in a patient with the device including a receiver with arms that are spaced apart that form a channel sized to receive the elongated member, and a groove on an inner surface of at least one of the arms. A shaft may be operatively connected to the receiver and configured to attach to the bone. A securing mechanism is attached to the receiver that includes an outer member and an inner member. The outer member may include a bore and a non-threaded exterior that may be configured to engage with the groove to attach the securing mechanism to the receiver. The second member may be sized to fit in the bore and move axially along the bore in a non-rotational manner. The second member may also include a compressible extension sized to fit in the bore when the extension is moved in the bore and to expand to a width greater than the bore when the second member extends outward beyond the bore.

17 Claims, 7 Drawing Sheets

U.S. PATENT DOCUMENTS

| | | | |
|---|---|---|---|
| 2006/0149233 A1* | 7/2006 | Richelsoph | 606/61 |
| 2006/0247636 A1* | 11/2006 | Yuan et al. | 606/61 |
| 2006/0276792 A1* | 12/2006 | Ensign et al. | 606/61 |
| 2007/0167949 A1* | 7/2007 | Altarac et al. | 606/61 |
| 2007/0225717 A1 | 9/2007 | Hawkes | |
| 2008/0243189 A1* | 10/2008 | Purcell et al. | 606/264 |
| 2009/0105770 A1* | 4/2009 | Berrevoets et al. | 606/308 |
| 2010/0114168 A1 | 5/2010 | Miller | |
| 2010/0241170 A1 | 9/2010 | Cammisa et al. | |
| 2010/0312279 A1* | 12/2010 | Gephart et al. | 606/264 |

* cited by examiner

ANCHOR WITH TWO MEMBER SECURING MECHANISM FOR ATTACHING AN ELONGATED MEMBER TO A BONE

RELATED APPLICATION

Co-pending U.S. patent application Ser. No. 12/261,253 is directed to an anchor with a non-threaded securing mechanism to attach an elongated member to a bone.

BACKGROUND

The present application relates to anchors for attaching an elongated member to a bone, and more particularly to anchors with a two member securing mechanism to prevent the elongated member from escaping from the anchor.

Elongated members such as but not limited to rods, wires, and tethers, are used in a variety of different surgical applications. The elongated members are attached to a bone in a patient and may provide a corrective force, support, or positioning for the bone and other adjacent bones. The elongated members are attached to the bone by anchors that include a receiver and a shaft. The receiver is configured to receive the elongated member, and the shaft is configured to attach to the bone. Many previous anchors include a set screw that is threaded onto the receiver to capture the elongated member. The threaded set screw design may include several drawbacks.

One drawback of a threaded set screw design is the set screw may be threaded improperly onto the receiver. This may cause the threads to be stripped on the receiver and/or set screw. The set screw may bind within the receiver preventing further tightening of the set screw to fully engage the elongated member. Alternatively, the set screw is thereafter removed from the receiver but the threads on the receiver are stripped requiring removal and replacement. Another issue may be the false impression that the set screw is fully tightened in the receiver and engaged with the elongated member. At some point thereafter, the improperly threaded set screw loosens in the receiver requiring a revision procedure.

Another drawback is the set screw may cause the arms of the receiver to splay apart. The set screw may apply an outward force on the arms of the receiver as it is threaded onto the receiver. This force may cause the arms to move apart which may cause the set screw to become loosely attached to the receiver. Again, this may result in the set screw not fully engaging the elongated member, and/or the set screw becoming loose which would require correction during a revision procedure.

SUMMARY

The present application is directed a device to attach an elongated member to a bone in a patient. The device may include a receiver with arms that are spaced apart that form a channel sized to receive the elongated member. The receiver may further include a groove on an inner surface of at least one of the arms. The device may also include a shaft operatively connected to the receiver and configured to attach to the bone. The device may also include a securing mechanism to attach to the receiver and includes an outer member and an inner member. The outer member may include a bore that extends through the outer member and a non-threaded exterior that may be configured to engage with the groove to attach the securing mechanism to the receiver. The second member may be sized to fit in and move axially along the bore in a non-rotational manner. The second member may also include a compressible extension that is sized to fit within the bore when the extension is moved in the bore and to expand to a width greater than the bore when the second member extends outward beyond the bore.

Other aspects of various embodiments of the anchor are also disclosed in the following description. The various aspects may be used alone or in any combination, as is desired.

DETAILED DESCRIPTION

Figure 1:
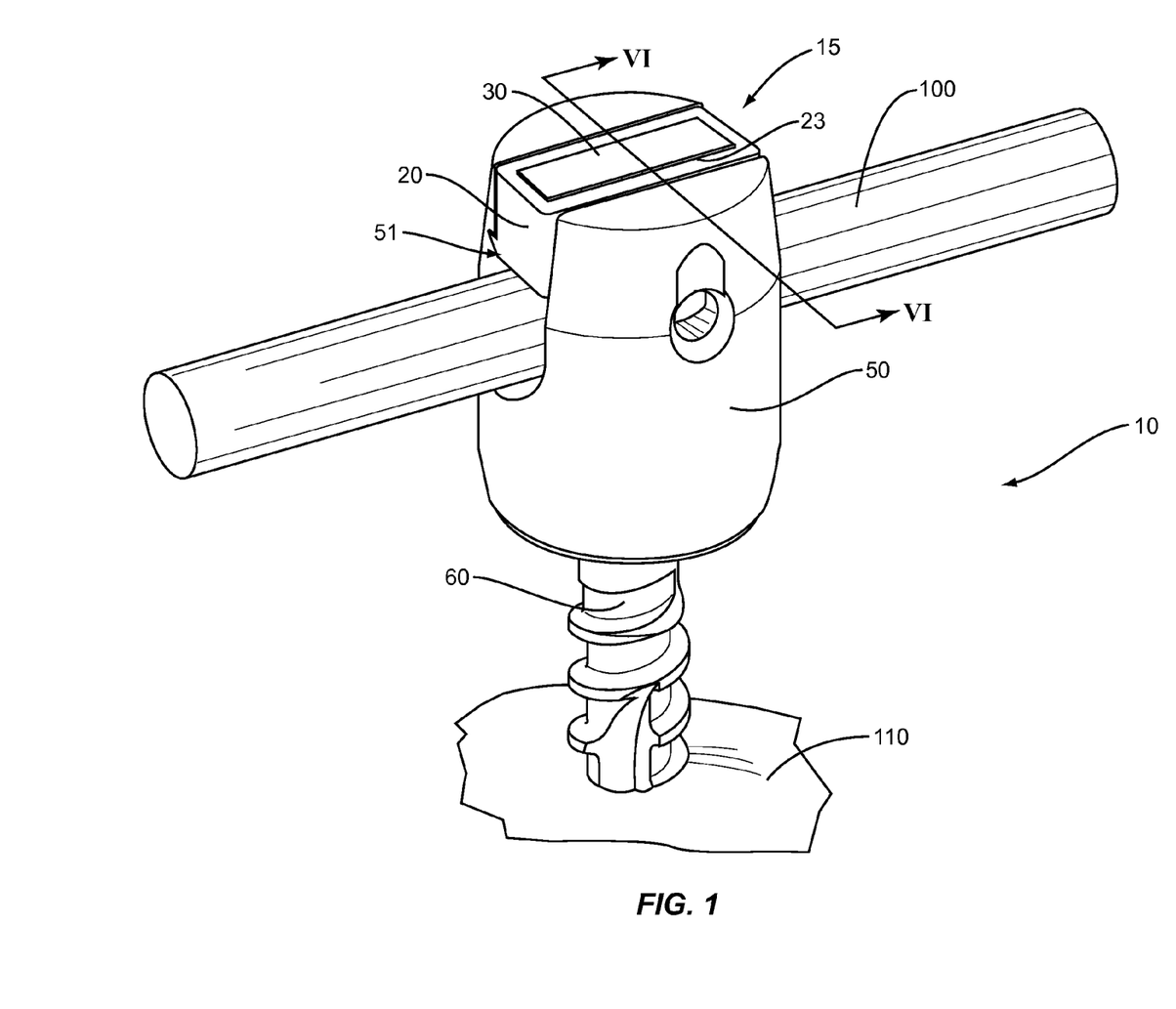
FIG. 1 is a perspective view of an anchor for attaching an elongated member to a bone according to one embodiment.

The present application is directed to an anchor with a non-threaded securing mechanism for attaching an elongated member to a bone. FIG. 1 illustrates one embodiment of an anchor 10 securing an elongated member 100 to a bone 110. The anchor 10 includes a receiver 50, shaft 60, and securing mechanism 15. The receiver 50 includes a channel 51 sized to receive the elongated member 100, and the shaft 60 is configured to engage with the bone 110. The securing mechanism 15 includes an outer member 20 and an inner member 30 and attaches to the receiver 50 to capture the elongated member 100 in the channel 51. The outer member 20 includes a bore 23 and a non-threaded exterior configured to engage with the receiver 50. The inner member 30 fits in and moves axially along the bore 23 in a non-rotational manner. The inner member 30 includes a compressible extension sized to fit in the bore 23 as the inner member 30 moves along the bore 23, and to expand to a width greater than the bore 23 when the extension is moved outward beyond the end of the outer member 20 towards the elongated member 100.

Figure 2:
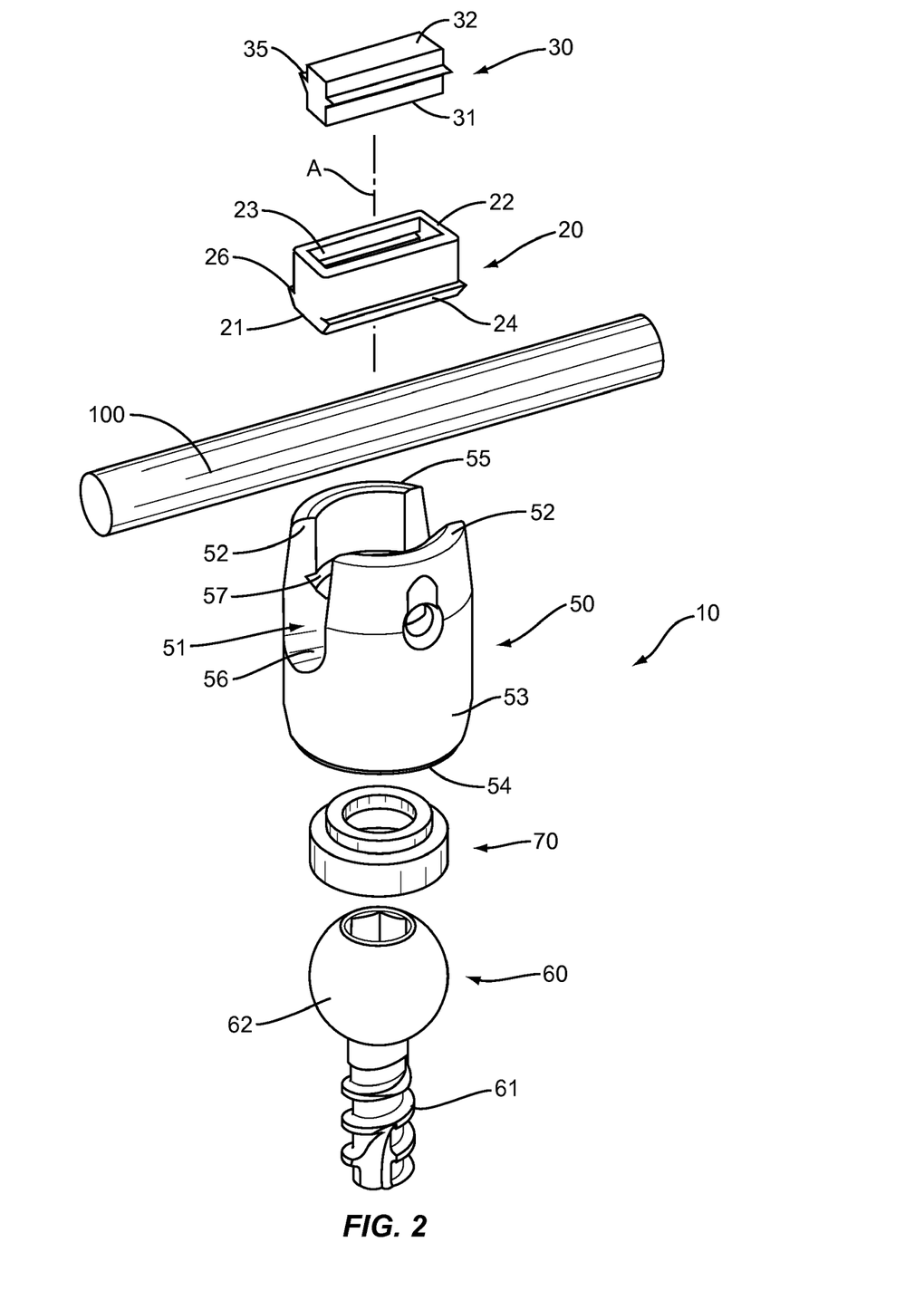
FIG. 2 is an exploded perspective view of an anchor for attaching an elongated member to a bone according to one embodiment.
Figure 3:
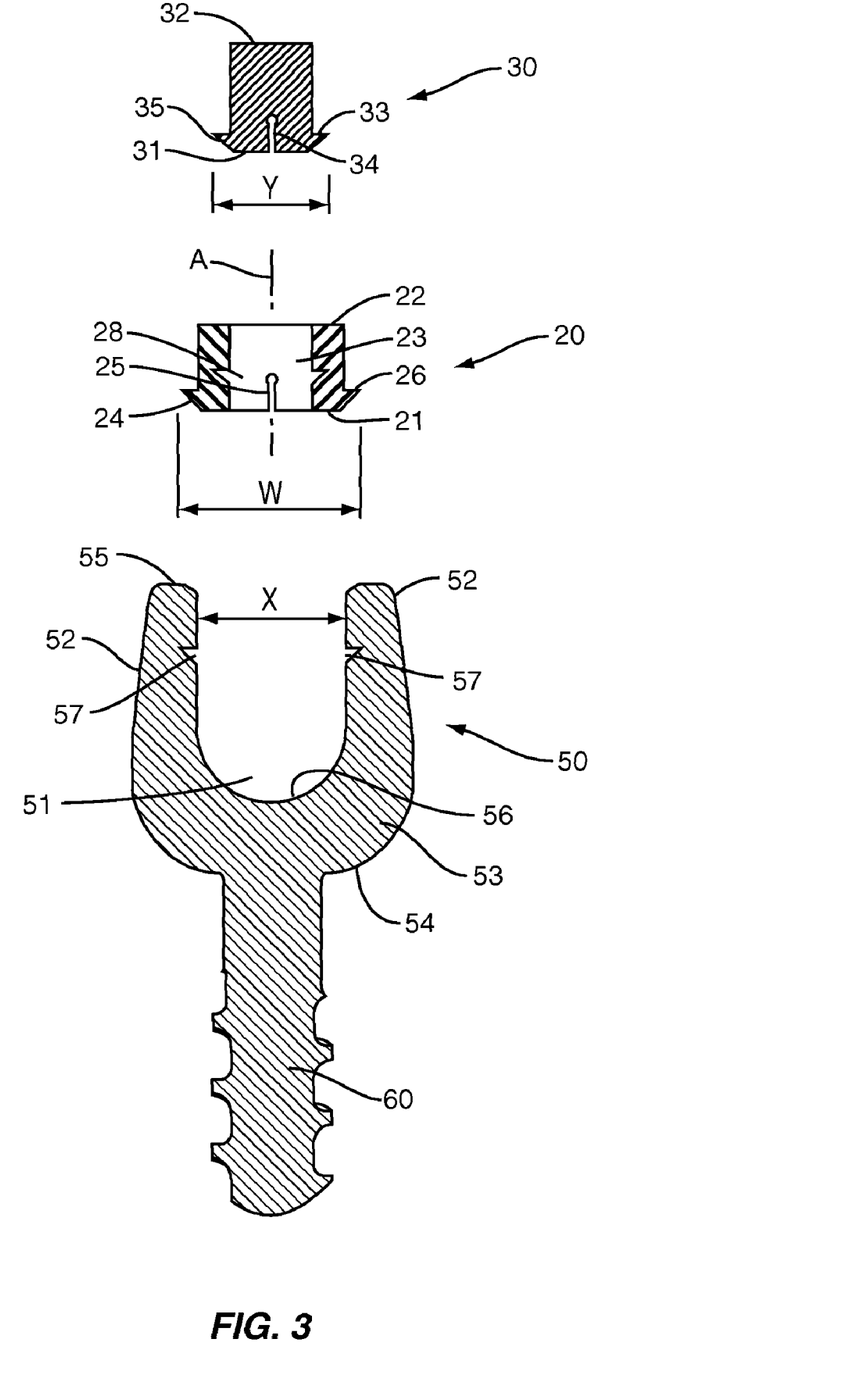
FIG. 3 is an exploded sectional view of an anchor for attaching an elongated member to a bone according to one embodiment.

As illustrated in FIG. 2, the receiver 50 includes a first end 54 and a second end 55. The channel 51 extends into the receiver 50 from the second end 55 and is formed by arms 52 and a base 53. A receiving surface 56 of the channel 51 may be shaped to match the size and shape of the elongated member 100. As illustrated in FIG. 3, one or more grooves 57 are positioned on an inner surface of the arms 52 that extend into the arms 52 away from the channel 51. The grooves 57 are shaped and sized to receive an extension 24 on the outer member 20 as will be explained in detail below. The groove 57 may be positioned on one or more of the arms 52 of the receiver 50.

The shaft 60 is configured to attach to the bone 110. The shaft 60 may include threads 61 that engage with the bone 110. Shaft 60 may also include a hook or other shape to engage with the bone 110

The receiver 50 and shaft 60 may be formed as a single piece as illustrated in FIG. 3. The receiver 50 and shaft 60 may also be separate pieces that are attached together. The two piece construction provides for the receiver 50 to be movable relative to the shaft 60 to accommodate the elongated member 100 at various angular positions. FIG. 2 includes an embodiment with the base 53 of the receiver 50 including a hollow interior sized to receive a head 62 of the shaft 60. A crown 70 may be positioned on the head 62 to facilitate placement and movement of the anchor 60 relative to the receiver 50. U.S. patent application Ser. No. 12/038,572 discloses embodiments of two piece construction and is herein incorporated by reference.

The outer member 20 fits in the channel 51 and attaches to the receiver 50. As illustrated in FIGS. 2 and 3, the outer member 20 includes a first end 21 and a second end 22 and may include a substantially cylindrical shape with a longitudinal axis A. An exterior surface of the outer member 20 may be substantially smooth. A bore 23 extends through the outer member 20 and is centered along the axis A. The inner surface of the inner member 20 may also be substantially smooth. An extension 24 is positioned at the first end 21 and is configured to engage with the grooves 57 of the receiver 50. The extension 24 may include a tapered shape with the largest width positioned towards the second end 22 and narrowing towards the first end 21. In one embodiment, the extension 24 includes a contact surface 26 that is substantially perpendicular to the longitudinal axis A. The embodiments of FIGS. 2 and 3 include a single continuous extension 24 that extends completely around the periphery of the outer member 20. In other embodiments, the extension 24 includes one or more discrete sections such that it is not continuous.

Figure 4:
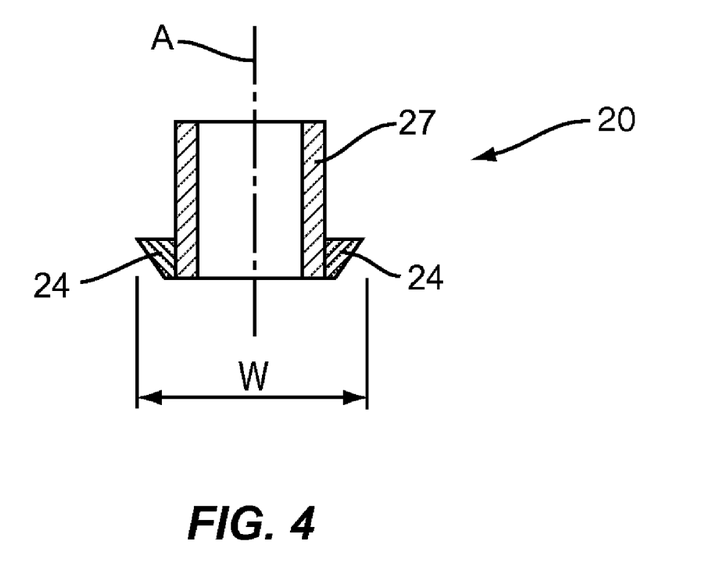
FIG. 4 is a sectional view of an outer member according to one embodiment.

The width W of the extension 24 may be greater than the width X of the channel 51 as illustrated in FIG. 3. To allow insertion of the outer member 20 into the receiver 50, the extension 24 is compressible to reduce the width W for insertion into the channel 51. The outer member 20 may include one or more slots 25 that extend inward from the first end 21. The slots 25 may include opposing side walls and an interior end and provide for the extension 24 to compress inward toward the longitudinal axis A while the extension 24 is in the bore 23. In another embodiment, the outer member 20 is constructed of a compressible material that compresses during insertion into the channel 51. FIG. 4 includes the outer member 20 with a body 27 constructed of a first material and extension 24 constructed of a compressible second material. The body 27 includes a width less than the width X of the channel 51, with just the extension 24 deforming to reduce the width W for insertion into the channel 51. The various embodiments provide for the extension 24 to rebound outward away from the longitudinal axis A when the extension 24 aligns with the groove 57 in the receiver 50.

The inner member 30 is sized to axially move along the bore 23 of the outer member 20. The inner member 30 includes a first end 31 and an opposing second end 32. The inner member 30 may be solid, or include a bore that extends through an interior section from the first end 31 to the second end 32. The inner member 30 may also be substantially solid with a cavity that extends inward from the first end 31 as illustrated in FIG. 3. The outer surface of the inner member 30 may be substantially smooth. An extension 35 is positioned at the first end 31 and includes a narrowing width that decreases toward the first end 31. The extension 35 may include a contact surface 33 that is substantially perpendicular with a longitudinal axis of the inner member 30. The extension 35 may extend continuously around the inner member 30, or may include one or more discrete sections.

The extension 35 includes a width Y that is greater than a width of the bore 23. The extension 35 is constructed to be compressed to reduce the width Y for insertion into the bore 23. One or more slots 34 may extend inward from the first end 31 and may include opposing sidewalls and an interior end. The slots 34 provide for the extension 35 to be compressed inward while positioned in the bore 23. In another embodiment, the extension 35 is constructed of a compressible material that compresses while in the bore 23. Similar to the outer member embodiment of FIG. 4, the inner member 30 includes a body constructed of a first material and extension 35 constructed of a compressible second material. The body includes a width less than the bore 23, with just the extension 35 deforming to reduce the width Y for insertion into the bore 23. In another embodiment, the entire inner member 30 is constructed of a compressible material. The extension 35 is constructed to rebound outward away from the longitudinal axis when the extension 35 moves beyond the first end 21 of the outer member 20.

Figure 5:
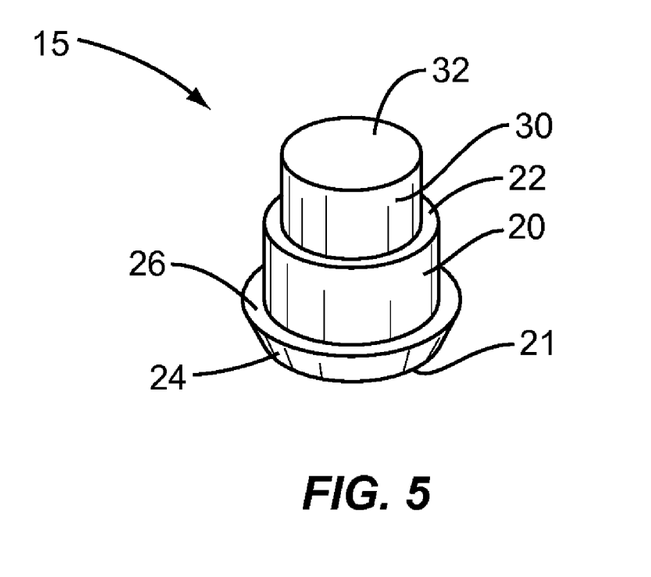
FIG. 5 is a perspective view of a securing mechanism according to one embodiment.
Figure 10:
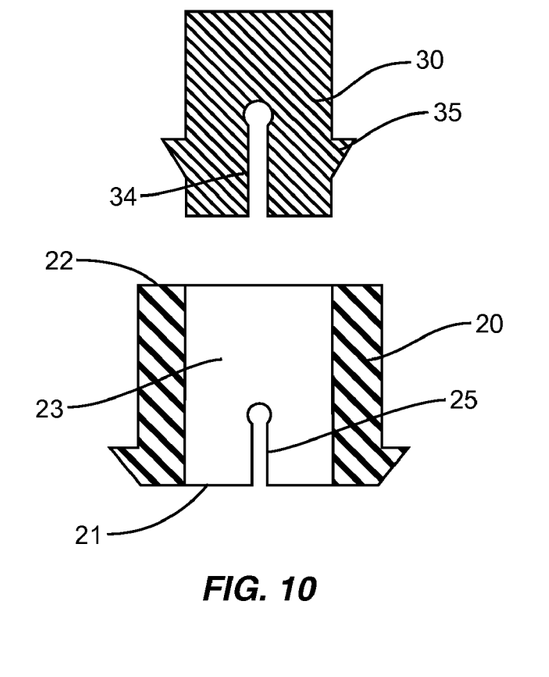
FIG. 10 is a section view of an outer member and an inner member according to one embodiment.

The outer member 20 may be operatively connected to the inner member 30 prior to attachment to the receiver 50. This facilitates attachment of the securing mechanism 15 to the receiver 50 by forming a larger overall structure that may be easier to handle by the surgeon during the surgical procedure. In one embodiment as illustrated in FIG. 3, a groove 28 is positioned on the inner surface of the outer member 20. The extension 35 of the inner member 30 engages within the groove 28 to attach the members 20, 30 together. FIG. 5 illustrates one embodiment of the inner member 30 attached to the outer member 20. The second end 32 of the inner member 30 extends outward beyond the second end 22 of the outer member 20 when the extension 35 is engaged with the grooves 28. In another embodiment, the expansion force of the compressed extension 35 against the inner surface of the outer member 20 is adequate for attaching together the members 20, 30. In this embodiment, the outer member 20 may not include a groove 28. FIG. 10 includes an embodiment with the surfaces of the outer and inner members 20, 30 being substantially smooth. The inner member 30 is press-fit into the bore 23 to pre-assemble the outer and inner members 20, 30. The outer member 20 without a groove 28 may include a smaller height between the first and second ends 21, 22 than one that includes a groove 28.

The outer member 20 and inner member 30 may be constructed of various materials. Examples include but are not limited to titanium, PEEK, polyurethane, polypropylene, or polyethylene, and UHMWPE. The extensions 24, 35 may also be constructed of these materials.

One method of using the anchor 10 includes attaching the receiver 50 and shaft 60 to the bone 110 at the appropriate position to receive the elongated member 100. Once the elongated member 100 is in the channel 51, the securing mechanism 15 is attached to receiver 50 to secure the elongated member 100. Initially, the outer member 20 is inserted into the channel 51. The tapered shape of the extension 24 at the first end 21 may facilitate alignment of the outer member 20 relative to the receiver 50, and insertion of the outer member 20 into the channel 51. Insertion of the outer member 20 causes the extension 24 to compress inward with a reduction in the width W. The outer member 20 is slid into the channel 51 until the extension 24 aligns with the groove 28 on the inner surface of the arms 52. Alignment causes the extension 24 to rebound outward away from the longitudinal axis A and into the groove 28. The shape of the groove 28 may match the shape of the extension 24.

Once the outer member 20 is attached to the receiver 50, the inner member 30 is axially moved along the bore 23. During the movement, the extension 35 is compressed inward and slides along the inner surface of the outer member 20. The inner member 30 is axially moved until the extension 35 moves beyond the first end 21 of the outer member 20. The extension 35 then rebounds outward away from the longitudinal axis A of the outer member 20 causing the width Y to increase and be greater than the width of the bore 23. This increased width prevents moving in the opposite direction (i.e., away from the elongated member 100). In one embodiment as illustrated in FIG. 6, the first end 32 of the inner member 30 contacts against the elongated member 100, and the first end 21 of the outer member 20 is spaced away from the elongated member.

Figure 6:
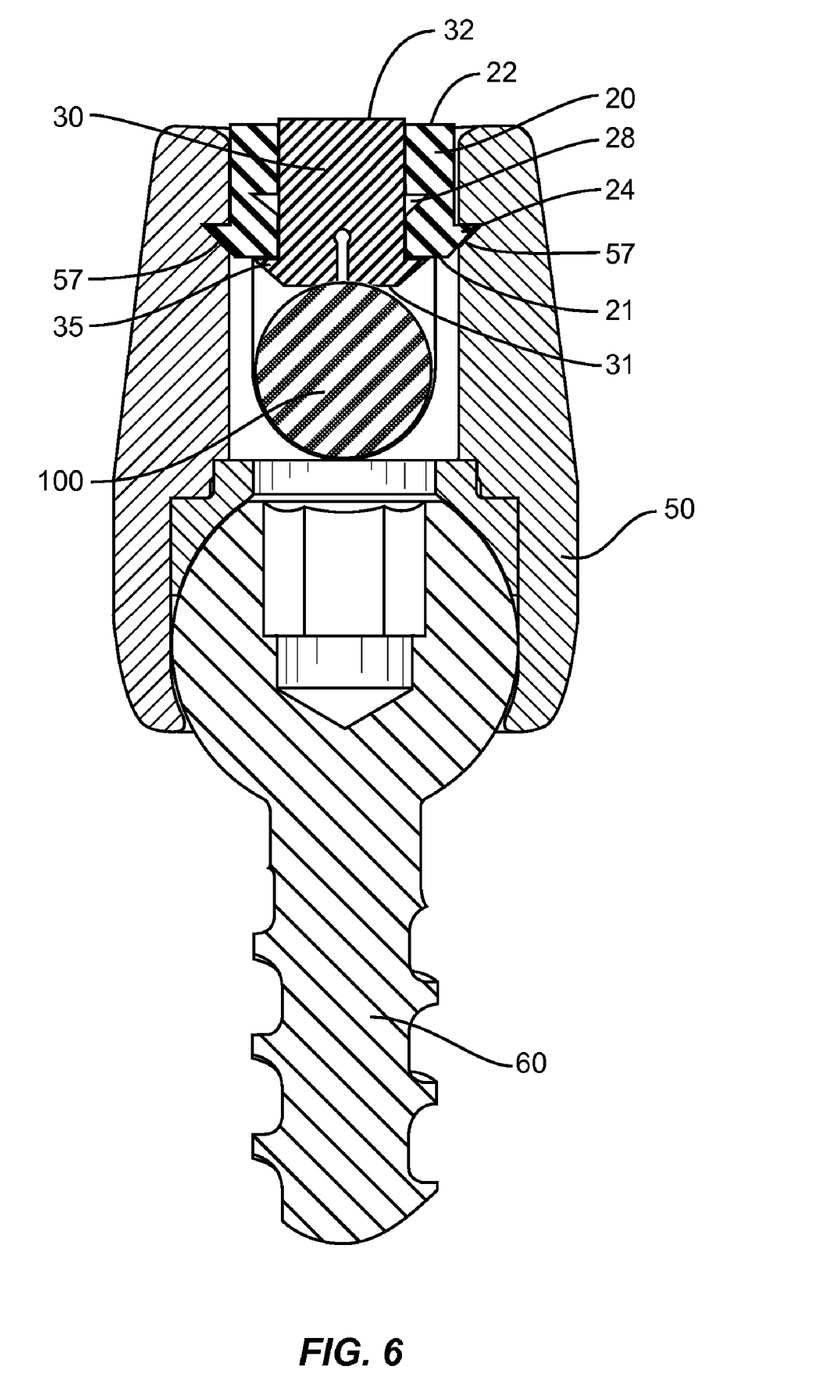
FIG. 6 is a sectional view cut along line VI-VI of FIG. 1 of an elongated member within an anchor according to one embodiment.

As illustrated in FIG. 6, the second end 22 of the outer member 20 and second end 32 of the inner member 30 may be flush with the second end 55 of the receiver 50. The length of the inner member 30 measured between the first and second ends 31, 32 may be longer than the outer member 20. This provides for the first end 31 to extend outward beyond the first end 21 of the outer member 20 and the second end 32 to be flush with the second end 22.

Figure 7:
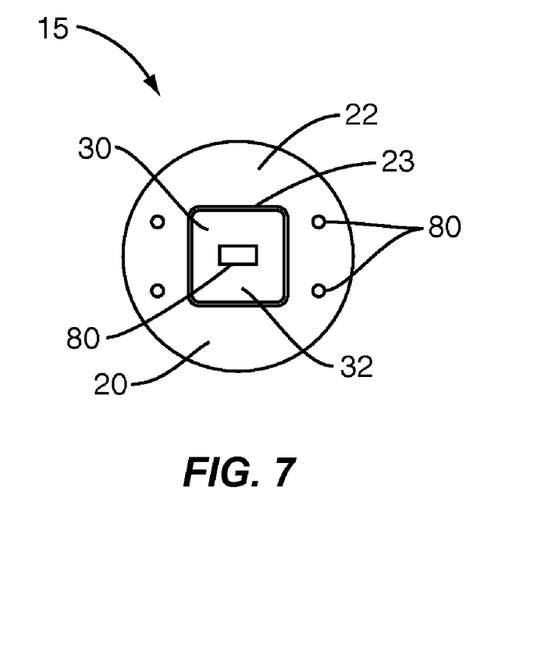
FIG. 7 is a top view of a securing mechanism with an outer member and an inner member according to one embodiment.

The force applied to the outer member 20 and inner member 30 may be directly applied by the surgeon. The surgeon may use their finger and/or hand to directly contact against the second ends 22, 32 and move the members 20, 30. Alternatively, the second ends 22, 32 may include receptacles 80 as illustrated in FIG. 7 to receive a tool that is handled by the surgeon and applies the force to the members 20, 30.

The cross-sectional shapes of the bore 23 and inner member 30 may substantially match to facilitate axial movement of the inner member 30 relative to the outer member 20. In one embodiment as illustrated in FIG. 1, the cross-sectional shapes are substantially rectangular. The cross-sectional shapes prevent the inner member 30 from rotating within the bore 23. Various other shapes may also be used to prevent rotation, including but not limited to square and triangle. FIG. 5 includes another embodiment with circular cross-sectional shapes.

Figure 11:
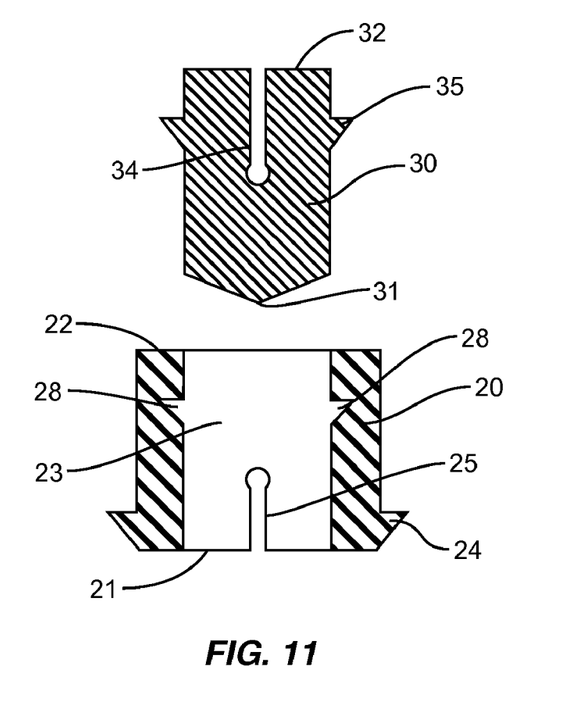
FIG. 11 is a section view of an outer member and an inner member according to one embodiment.

The extension 24 may be located at various points along the outer member 20 between the first and second ends 21, 22. FIGS. 2 and 3 include the extension 24 positioned at the first end 21. Other embodiments may include the extension 24 positioned at an intermediate location, and at the second end 22. The extension 35 may also be located at various points along the inner member 30. FIG. 11 includes the outer member 20 including grooves 28 in proximity to the second end 22. The inner member 30 includes extensions 35 positioned towards the second end 32 to mate with the grooves 28 during insertion into the bore 23. The inner member 30 further includes a slot 34 extending inward from the second end 32 to allow for compression of the extensions 35 during insertion in to the bore 23.

FIG. 11 also includes a non-compressible section of the inner member 30 being aligned with the extensions 24 of the outer member 20 when the inner member 30 is attached to the outer member 20. This prevents the extensions 24 from compressing after being attached to the receiver 50.

Figure 8:
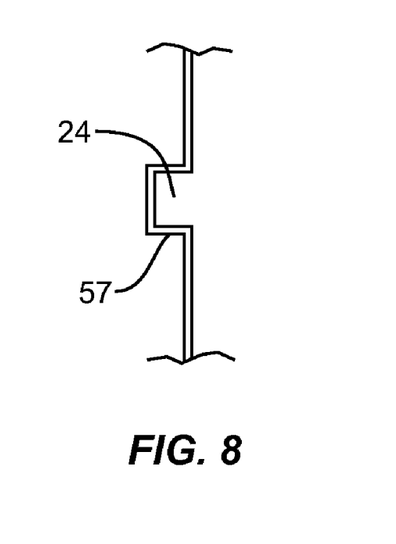
FIG. 8 is a partial side view of an extension of an outer member positioned within a groove of a receiver according to one embodiment.
Figure 9:
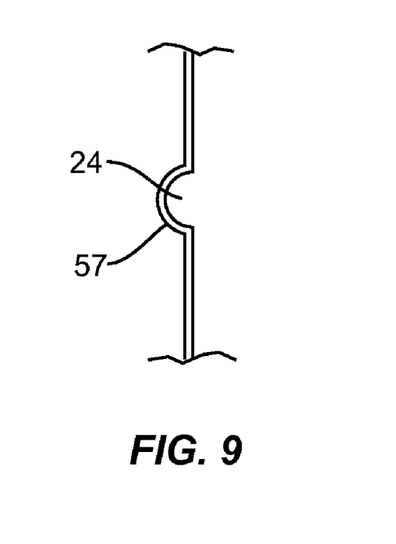
FIG. 9 is a partial side view of an extension of an outer member positioned within a groove of a receiver according to one embodiment.

The shapes of the groove 57 may match the shape of the extension 24. FIG. 3 includes an embodiment with each including an angular shape. The shapes may also provide for movement of the outer member 20 into the channel 51 and prevent movement away from the channel 51. By way of example and using FIG. 3, the groove 57 includes a contact surface 26 that is substantially perpendicular with a longitudinal axis of the receiver 50. The contact surface 26 of the outer member 20 is substantially perpendicular with the longitudinal axis of the outer member 20. These shapes and configurations prevent the outer member 20 from moving away from the channel 51 once the outer member 20 is attached to the receiver 50. FIGS. 8 and 9 illustrate other embodiments of the grooves 57 and extensions 24. In embodiments with extensions 24 including multiple discrete sections, the extensions 24 may include the same or different shapes.

The elongated member 100 may include a variety of configurations, including but not limited to a rod, wire, and tether. The elongated member 100 may be made from a suitably strong rigid material known in the art, such as titanium, or from a semi-rigid material such as PEEK, polyurethane, polypropylene, or polyethylene. The elongated member 100 may include a variety of cross-sectional shapes including but not limited to circular, rectangular, square, and oval. Depending upon the context of use, the elongated member 100 may be linear or non-linear.

The elongated member 100 provides a force to the bone 110. One application includes the elongated member 100 being applied to the spine of a patient with the bone 110 being a vertebral member. In one specific embodiment, the anchor 10 is attached to a pedicle of a vertebral member. Other applications include but are not limited to attachment to the femur, fibula, tibia, humerus, and mandible.

The present invention may be carried out in other specific ways than those herein set forth without departing from the scope and essential characteristics of the invention. Further, the various aspects of the disclosed device and method may be used alone or in any combination, as is desired. The disclosed embodiments are, therefore, to be considered in all respects as illustrative and not restrictive, and all changes coming within the meaning and equivalency range of the appended claims are intended to be embraced therein.

What is claimed is:

1. A device to attach an elongated member to a bone in a patient, the device comprising:

a receiver with a pair of spaced-apart arms that form a channel sized to receive the elongated member and a groove on an inner surface of at least one of the spaced-apart arms;

a shaft operatively connected to the receiver and configured to attach to the bone; and a securing mechanism to attach to the receiver and capture the elongated member in the channel, the securing mechanism including a first member and a second member with the first member including a non-threaded exterior and being configured to engage with the groove to attach the securing mechanism to the receiver and including a bore that extends from a first end to a second end, the second member sized to fit within the bore and including a non-threaded exterior with a compressible extension;

the second member including first and second ends and a size and shape to axially move along the bore with non-rotational movement from a first axial position with the extension positioned in the bore in a compressed orientation and including a first width and a second axial position in closer proximity to the shaft with the extension including a second width greater than the first width;

the first member including a second compressible extension that extends outward from the non-threaded exterior and is movable between a compressed position and an expanded position with the expanded position configured to extend into the groove to attach the securing mechanism to the receiver;

the second member being in closer proximity to the channel when the extension of the second member is at the second width.

2. The device of claim 1, wherein the extension of the second member is positioned outward beyond the first end of the first member and into the channel in the second position.

3. The device of claim 1, wherein the extension of the second member is positioned at the first end of the second member and includes a contact surface that is substantially perpendicular to a longitudinal axis of the second member.

4. The device of claim 1, wherein the non-threaded exterior of the second member and an inner surface of the first member are smooth.

5. The device of claim 1, wherein the second member includes one or more slots that extend inward from one of the first and second ends and include opposing sidewalls and an interior end.

6. The device of claim 1, wherein the second ends of the first and second members are substantially flush with a second end of the receiver when the first member is attached to the receiver and the second member is in the second position.

7. The device of claim 1, wherein the second end of the second member extends outward from the bore beyond the second end of the first member when the second member is in the first position.

8. The device of claim 1, wherein the extension of the second member extends completely around the second member.

9. The device of claim 1, wherein the bore and the second member each include a rectangular cross-sectional shape.

10. A device to attach an elongated member to a bone in a patient, the device comprising:

a receiver with arms that are spaced apart and form a channel sized to receive the elongated member, the receiver further including a groove on an inner surface of at least one of the arms;

a shaft operatively connected to the receiver and configured to attach to the bone; and a securing mechanism to attach to the receiver and including an outer member and an inner member, the outer member including a bore that extends through the outer member and a non-threaded exterior configured to engage with the groove on the inner surface of at least one of the arms to attach the securing mechanism to the receiver, the second member sized to fit in the bore and including a shape to move axially along the bore in a non-rotational manner, the second member including a compressible extension sized to fit in the bore when the second member is moved along the bore and to expand to a width greater than the bore when the extension is positioned outward beyond the bore;

the extension being in closer proximity to the channel when the extension is expanded and positioned outward beyond the bore;

wherein the bore of the outer member and an exterior of the inner member include rectangular cross-sectional shapes.

11. The device of claim 10, wherein the extension includes a contact surface that is substantially perpendicular to a longitudinal axis of the inner member.

12. The device of claim 10, wherein the extension is positioned at an end of the inner member.

13. The device of claim 10, wherein the first member includes a second compressible extension that extends outward from the non-threaded exterior, the second compressible extension movable between a compressed first position and an expanded second position, the second compressible extension configured to fit in the groove of the receiver in the expanded second position.

14. A method of attaching an elongated member to a bone in a patient comprising:

inserting in a non-rotational manner a first member into a channel of the receiver with an extension of the first member being compressed radially inward;

inserting the first member farther into the channel of the receiver and expanding the extension of the first member radially outward into a groove in the receiver and attaching the first member to the receiver thereby positioning the elongated member in the channel between a base of the receiver and the first member, the receiver being attached to the bone;

moving in a non-rotational manner towards the elongated member a second member along a bore in the first member with an extension on the second member moving through the bore; and moving the second member farther along the bore in the non-rotational manner towards the elongated member and moving the extension of the second member beyond an end of the bore where the extension of the second member expands to a width that is greater than the bore;

the extension of the second member being in closer proximity to the channel when the extension of the second member is expanded and positioned outward beyond the end of the bore.

15. The method of claim 14, further comprising attaching the first member to the receiver and positioning the first member away from the elongated member and moving the extension of the second member beyond the end of the bore and contacting the second member against the elongated member.

16. The method of claim 14, further comprising aligning upper edges of the first and second members with an upper edge of the receiver when the extension of the second member moves beyond the end of the bore.

17. The method of claim 14, further comprising moving the extension of the second member beyond the end of the bore and maintaining a section of the second member within the bore.

* * * * *